US007061623B2

(12) United States Patent
Davidson

(10) Patent No.: US 7,061,623 B2
(45) Date of Patent: Jun. 13, 2006

(54) INTERFEROMETRIC BACK FOCAL PLANE SCATTEROMETRY WITH KOEHLER ILLUMINATION

(75) Inventor: Mark P. Davidson, Palo Alto, CA (US)

(73) Assignee: Spectel Research Corporation, Palo Alto, CA (US)

( * ) Notice: Subject to any disclaimer, the term of this patent is extended or adjusted under 35 U.S.C. 154(b) by 0 days.

(21) Appl. No.: 10/647,742

(22) Filed: Aug. 25, 2003

(65) Prior Publication Data
US 2005/0046855 A1 Mar. 3, 2005

(51) Int. Cl.
G01B 9/02 (2006.01)
(52) U.S. Cl. ..................................... 356/497
(58) Field of Classification Search ............... 356/451, 356/497, 511, 512, 514
See application file for complete search history.

(56) References Cited

U.S. PATENT DOCUMENTS 2,612,074 A * 9/1952 Mirau ......................... 356/497
5,112,129 A * 5/1992 Davidson et al. ........... 356/497
5,398,113 A * 3/1995 de Groot .................... 356/497
6,545,763 B1 * 4/2003 Kim et al. ................... 356/497

OTHER PUBLICATIONS

See et al , Scanning optical microellipsometer for pure surface profiling, Applied Optics, Dec. 1996, pp. 6663-6668.*
Feke et al., Interferometric Back Focal Plane Microellipsometry, Applied Optics/ vol. 33, No. 101 Apr. 1, 1998 p. 1746.

* cited by examiner

Primary Examiner—Samuel A. Turner
(74) Attorney, Agent, or Firm—Michael L. Sherrard

(57) ABSTRACT

An interference spectroscopy instrument provides simultaneous measurement of specular scattering over multiple wavelengths and angles. The spectroscopy instrument includes an interference microscope illuminated by Koehler illumination and a video camera located to image the back focal plane of the microscope's objective lens while the path-length difference is varied between the reference and object paths. Multichannel Fourier analysis transforms the resultant intensity information into specular reflectivity data as a function of wavelength. This multitude of measured data provides a more sensitive scatterometry tool having superior performance in the measurement of small patterns on semiconductor devices and in measuring overlay on such devices.

34 Claims, 9 Drawing Sheets specimen is mounted on a moveable stage capable of vertical motion in the diagram

*Image of back aperture as seen by the video camera.
Different pixels see the light which strikes the object at different angles*

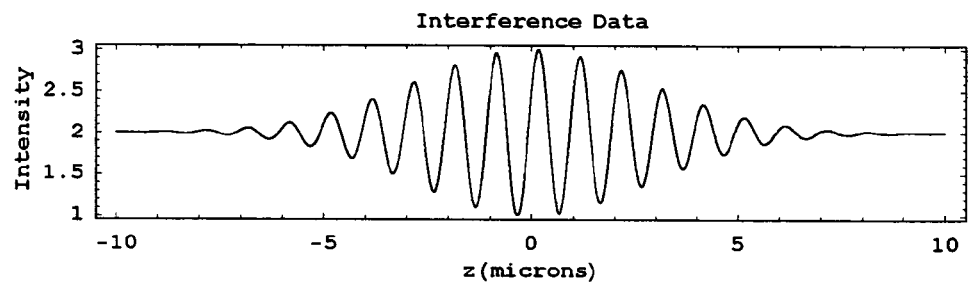
*Figure 6a*
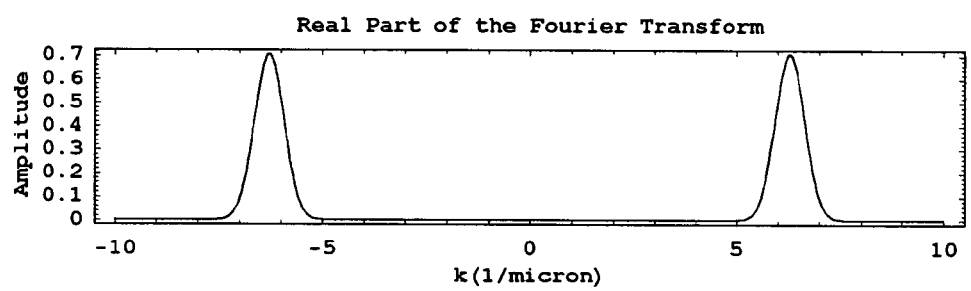
*Figure 6b*
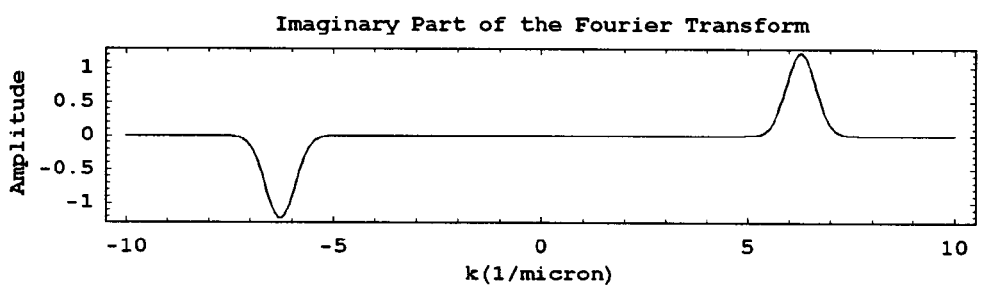
*Figure 6c*
*Figure 6*

INTERFEROMETRIC BACK FOCAL PLANE SCATTEROMETRY WITH KOEHLER ILLUMINATION

FIELD OF THE INVENTION

The present invention relates to field of optical scatterometry. More particularly, the present invention combines an interference microscope with Fourier transform spectroscopy to provide a multi-channel spectroscopy instrument for simultaneously measuring light reflected from multiple illumination angles at a plurality of wavelengths. The invention has particular applicability in the testing of semiconductor devices.

BACKGROUND

Scatterometry is an optical technique which uses the optical properties of scattered light to determine physical attributes of a sample. More specifically, scatterometry is used in the field of semiconductor testing to monitor the line width and line shape of patterns on semiconductor wafers. This is accomplished by forming a test structure including an array of lines on the semiconductor wafer. Typically the test structure is a diffraction grating some tens of microns on a side, but other structures can be used. Light is directed to the test structure and the light reflected from the test structure is measured at different wavelengths and scattering angles. These measurements are recorded and provide an optical "signature" of the test structure. This signature is then compared to a library of signatures for known structures, in a technique referred to as "inverse scattering." The library of known structures may be determined either by measurement or modeling. When the test data correlates to a signature of a known structure, the physical attributes of the test structure are assumed to be the similar to those of the corresponding known structure. As an example, a certain signature might indicate that the edges are rounded and that the line widths have a specific dimension. In this manner, the unknown physical attributes of a test structure are determined from the optical properties of the light scattered from it.

Scatterometry is becoming increasingly important as a method for accurately measuring the dimensions, shape and overlay registration of diffraction gratings on semiconductor devices. Scatterometry is used for measuring film thickness, measuring optical parameters of thin films, and measuring the dimensions of arrays of contact holes on semiconductor devices. Further still, scatterometry is used in metrology to provide control feedback in various manufacturing processes for integrated circuits, including both lithography and etching processes.

Current scatterometers are not capable of simultaneously measuring scattering data at multiple angles and wavelengths. In one type, a single illumination wavelength is provided by a laser beam and scattering data is generated one angle at a time by mechanically changing the angle of the illuminating laser beam while simultaneously moving the detector to receive the specularly reflected light. In another type, illumination is at a fixed angle (or a narrow cone of fixed angles) and the illumination is over a range of wavelengths. In another type, an ellipsometer is used to collect scatterometry data. In yet another type, broad-band illumination is used at a small cone angle of illumination angles, and the angle of incidence and the detector location are varied to acquire data for a multiple of angles.

Examples of the background and prior art include:

| 4,199,219 | April 1980 | Suzki et al. | 356/445 |
|---|---|---|---|

This is an early patent on the idea of optically scanning a light beam across a pattern on a wafer and detecting the reflected intensities for the purpose of measuring geometrical parameters of a pattern.

| 4,583,858 | April 1986 | Lebling et al. | 356/446 |
|---|---|---|---|

In this patent a method is described for illuminating an object with beams oriented at a number of different angles relative to the normal and with the ability to switch some of the channels off and on in order to avoid confusion in the final detector.

| 4,710,642 | December 1987 | McNeil | 250/571 |
|---|---|---|---|

A laser beam illuminates the object at a single angle of incidence, and scattered radiation is detected at a multitude of angles.

| 4,806,018 | February 1989 | Falk | 356/446 |
|---|---|---|---|

In this patent, light from a single point in the back focal plane of a lens illuminates an object with a collimated beam at an angle relative to normal. Different detectors are used to detect the scattered radiation at a plurality of angles.

| 5,164,790 | November 1992 | McNeil et al. | 356/445 |
|---|---|---|---|

A laser beam illuminates a diffraction grating object at a fixed angle, and diffracted light is detected. Results are compared with simulated diffraction models to provide calibration.

| 5,241,369 | August 1993 | McNeil et al. | 356/445 |
|---|---|---|---|

This patent shows a technique for measuring the non-specular scattering off of an object which is illuminated by a collimated beam.

| 5,539,571 | July 1996 | Cabib et al. | 392/019 |
|---|---|---|---|

A spectral decomposition of each pixel of an object is created by means of Fourier transform spectroscopy. Does not use a two-beam interference microscope. Rather, the light emitted from an object is split into two beams downstream in the output channel and each pixel is analyzed in a Fourier Transform spectroscopic system to determine the spectral emission of each pixel separately. In this system the interference beam splitting occurs after the light has scattered off of the object. In an interference microscope the interference beam splitting occurs before the light hits the object.

| 5,633,714 | May 1997 | Nyyssonen | 359/225 |

This patent describes an interference microscope system having a narrow angle, single wavelength, polarized illumination. The Fourier transforms mentioned in this patent are spatial Fourier transforms performed in the image space and not path length Fourier transforms as used in Fourier spectroscopy. The complex amplitudes (i.e. phase and amplitudes) of the scattered fields are measured in the vicinity of the focus plane of the microscope system, and not at the back focal plane. In this system, the object itself is imaged and not the back focal plane of the objective lens. This technology cannot eliminate the confusion regarding which illumination angle caused scattering into which output angle, and therefore it cannot be used to measure the specular reflectivity amplitudes for a non-specular object like a diffraction grating without limiting in some way the illumination angles.

| 5,703,692 | December 1997 | McNeil et al. | 356/445 |

An opto-mechanical means for changing the angle of incidence of a collimated beam on an object as a function of time. A single angle of incidence is measured at one time.

| 5,856,871 | January 1999 | Cabib et al. | 356/346 |

This patent uses spectral imaging of the type shown in U.S. Pat. No. 5,539,571 for film thickness measurement. Since for uniform films there is no non-specular scattering, there is no confusion regarding which output angle came from which input angle.

| 5,867,276 | February 1999 | McNeil et al. | 356/445 |

In this patent, the angle of incidence is changed by activating a mechanical stage to rotate the object, and the reflected specular light is analyzed in a spectrometer.

| 5,912,741 | June 1999 | Carter et al. | 356/445 |

This patent shows a novel beam steering system for illuminating the object at one angle at a time and collecting both diffuse and specular reflected light.

| 5,963,329 | October 1999 | Conrad et al. | 356/372 |

This is a broad scatterometry patent utilizing reflectometry, but it does not include an interference microscope or provide for measurement of interference images of a back focal plane from which can be deduced the specular reflection amplitudes that are shown in the current patent.

| 5,923,423 | July 1999 | Sawatari et al. | 356/484 |

This is a defect finding system which utilizes a two beam interference design, but is not a Mirau or Likik configuration. Rather, this system is teaches the use of oblique angles of illumination. Particles are detected by measuring interference between forward scattering and back scattering. The Doppler shift of a moving particle on a wafer is used as a phase shifting mechanism for observing the interference.

| 6,429,943 | August 2002 | Opsal et al. | 356/625 |

This patent shows illumination over a multitude of angles and also a multitude of wavelengths. However, it does not contain an interference microscope. Only reflected intensities can be measured and not complex amplitudes, and the illumination aperture must be restricted if confusion is to be avoided between specular and non-specular reflections in some cases.

Two general references on Fourier spectroscopy are: Vanasse, G. A., Sakai, H., "Fourier Spectroscopy," in *Progress in Optics* Volume VI, Edited by E. Wolf, North-Holland Publishing, Amsterdam, 1967, pages 259–330, and Steel, W. H., *Interferometry*, Cambridge University Press, London and New York, Second edition, 1983.

It is desirable to collect scattering data for a wide range of wavelengths and over a range of scattering angles. It is further desirable to do this quickly with an apparatus that has a minimum number of moving parts. Further still, it is desirable to illuminate the sample at multiple angles and wavelengths simultaneously in order to provide for a faster test. However, if the sample is illuminated at many angles at once, it is difficult to determine the intensity of the specular radiation measured by a detector. This is because light scatters in both specular and non-specular modes. That is, light incident from a given angle scatters in two modes. First, it scatters in a specular mode, where the angle of reflection equals the angle of incidence. Second, it scatters in a non-specular mode, where the angle of reflection is different from the angle of incidence. Thus, light received by a detector may include both light scattered in the specular mode from one incident angle and light scattered in a non-specular mode from a different incident angle. However, it is necessary to distinguish the specular terms from the non-specular terms in the data in order to develop an accurate "signature" for the sample. Since it is difficult to distinguish light scattered in a specular mode from light scattered in a non-specular mode, spectrometers typically illuminate a sample at only one incident angle (or a narrow range of incident angles) at a time. If the detector is then positioned to receive only light reflected at this one angle, only light reflected in a specular mode would be detected. However, this adds time to the detection process and complexity to spectrographic instrument since it must include a mechanism for varying the angle of the illumination and/or detection if multiple angles are to be measured.

It is therefore an object of the invention to provide a scatterometer system that enables multiple illumination angles to be measured simultaneously while obtaining amplitude data for each angle of illumination and for a range of wavelengths.

It is a further an object of the invention to measure scattering data at multiple angles and multiple wavelengths simultaneously without the need to reposition the optical components or the object.

It is a further object of the invention to measure phase and polarization dependence of the specular scattering data.

SUMMARY OF THE INVENTION

The preferred embodiment of the present invention is a lens scatterometry system that provides for a sample to be illuminated over multiple angles and wavelengths simultaneously. The specular (or "zero-order diffraction") data is determined for all angles and wavelengths simultaneously without confusion with non-specular terms. This is achieved through the combination of an interference microscope utilizing Koehler illumination and a video camera viewing the back focal plane of the microscope objective lens. The path-length difference between the object and reference paths in the interference microscope is varied while a sequence of optical images are captured by the video camera.

Each location on the image is processed as a separate channel and is transformed by Fourier analysis to provide the specular reflection coefficient terms as a function of angle and wavelength. This provides a spectroscopic signature useful in inverse signature or other types of spectroscopic analysis. Further, the current invention also provides phase and polarization data as a function of wavelength and angle.

BRIEF DESCRIPTION OF THE FIGURES

FIG. 6a is an illustration of the intensity data from a typical channel as a function of path-length-difference.

FIG. 6b is an illustration real part of the Fourier transform of the intensity data from of FIG. 6a.

FIG. 6c is an illustration imaginary part of the Fourier transform of the intensity data from of FIG. 6a.

DETAILED DESCRIPTION OF THE INVENTION

Figure 1:
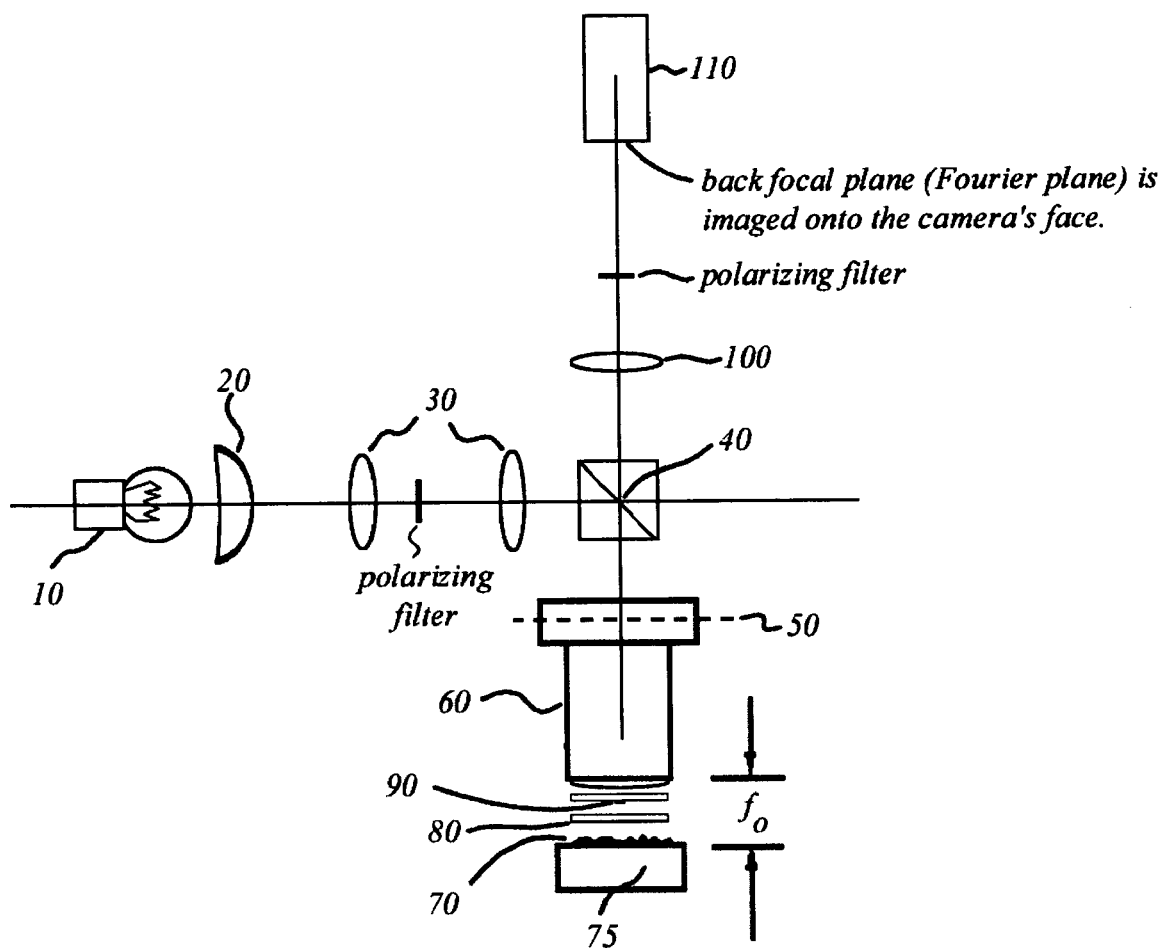
FIG. 1 is an illustration of a Mirau interference microscope adapted in accordance with one embodiment of the present invention.

FIG. 1 is an illustration of a Mirau interference microscope adapted in accordance the present invention. A light source 10 provides broadband illumination for the microscope. Light source 10 is a highly incoherent luminous source such as an arc lamp or a tungsten halogen lamp. Light source 10 is directed to and imaged on back focal plane 50 of microscope objective lens 60 by condenser lens 20, lenses 30, and beamsplitter 40.

Imaging a highly incoherent light source on back focal plane 50 in this manner provides a type of illumination known as Koehler illumination to the back focal plane 50 of the microscope. Koehler illumination is characterized by a minimum of spatial coherence between any two points on back focal plane 50. That is, in Koehler illumination, the mutual coherence function is nearly zero for any spaced-apart two points on back focal plane 50.

Figure 2:
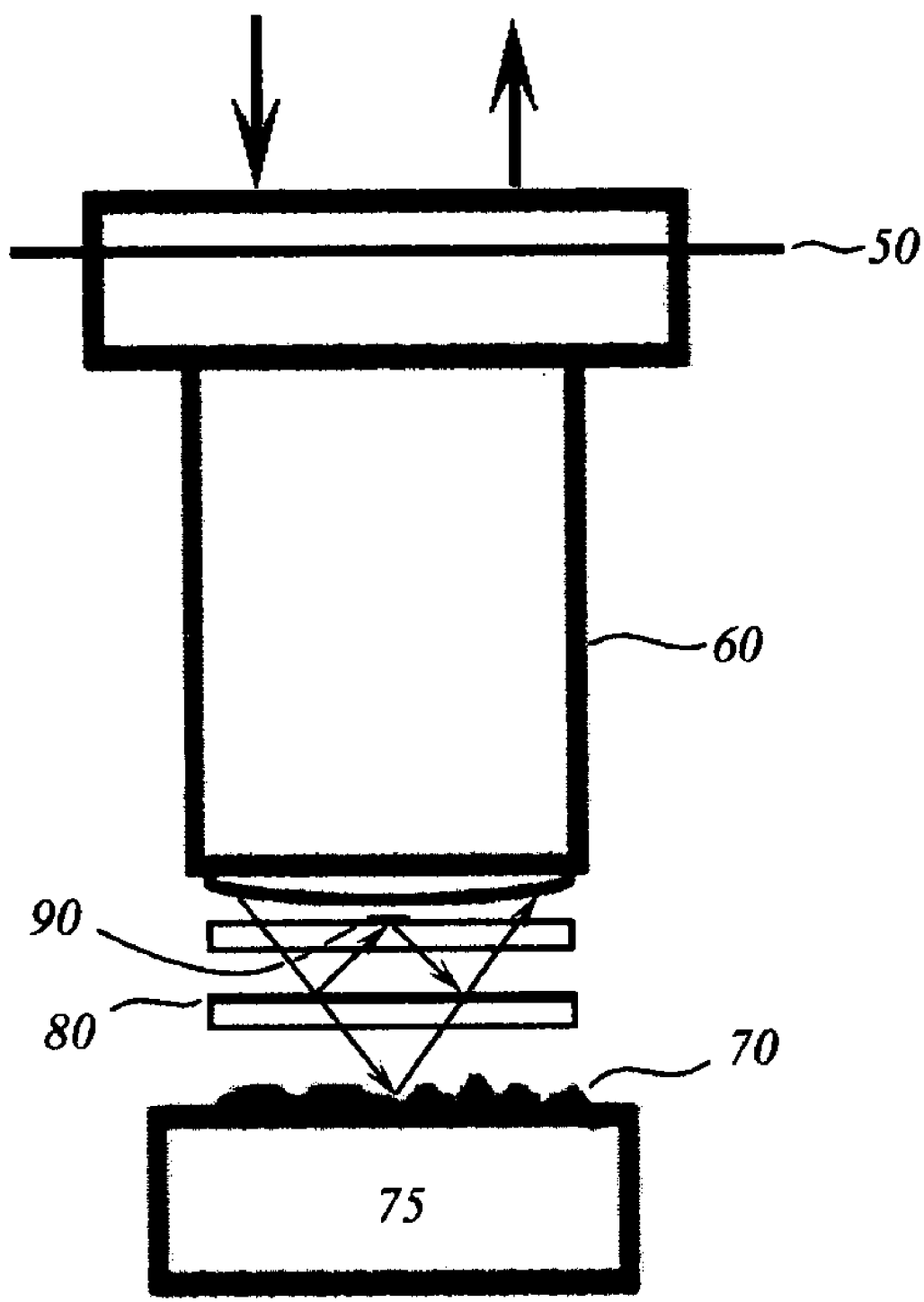
FIG. 2 is a more detailed illustration of the optical reference and object paths of the Mirau interference microscope shown in FIG. 1.

The optical reference path of the Mirau interference microscope is shown in FIG. 1 and again, in more detail, in FIG. 2. The Koehler illumination from back focal plane 50 is imaged by objective lens 60 onto reference mirror 90 after being reflected from Mirau beamsplitter 80. The optical reference path then reflects again from Mirau beamsplitter 80, and returns through objective lens 60 to back focal plane 50.

The optical object path of the Mirau interference microscope is also shown in FIG. 1 and again, in more detail, in FIG. 2. As illustrated, Koehler illumination from back focal plane 50 is imaged by objective lens 60 onto object plane 70 after passing through Mirau beamsplitter 80. The optical object path then returns through Mirau beamsplitter 80 and objective lens 60 to back focal plane 50.

As is typical in interference microscopes, the path-length difference between the object and reference paths is variable. In the present embodiment, the object (or "specimen") is mounted on a vertically moveable stage 75 that allows variation in the object path length.

Figure 3A:
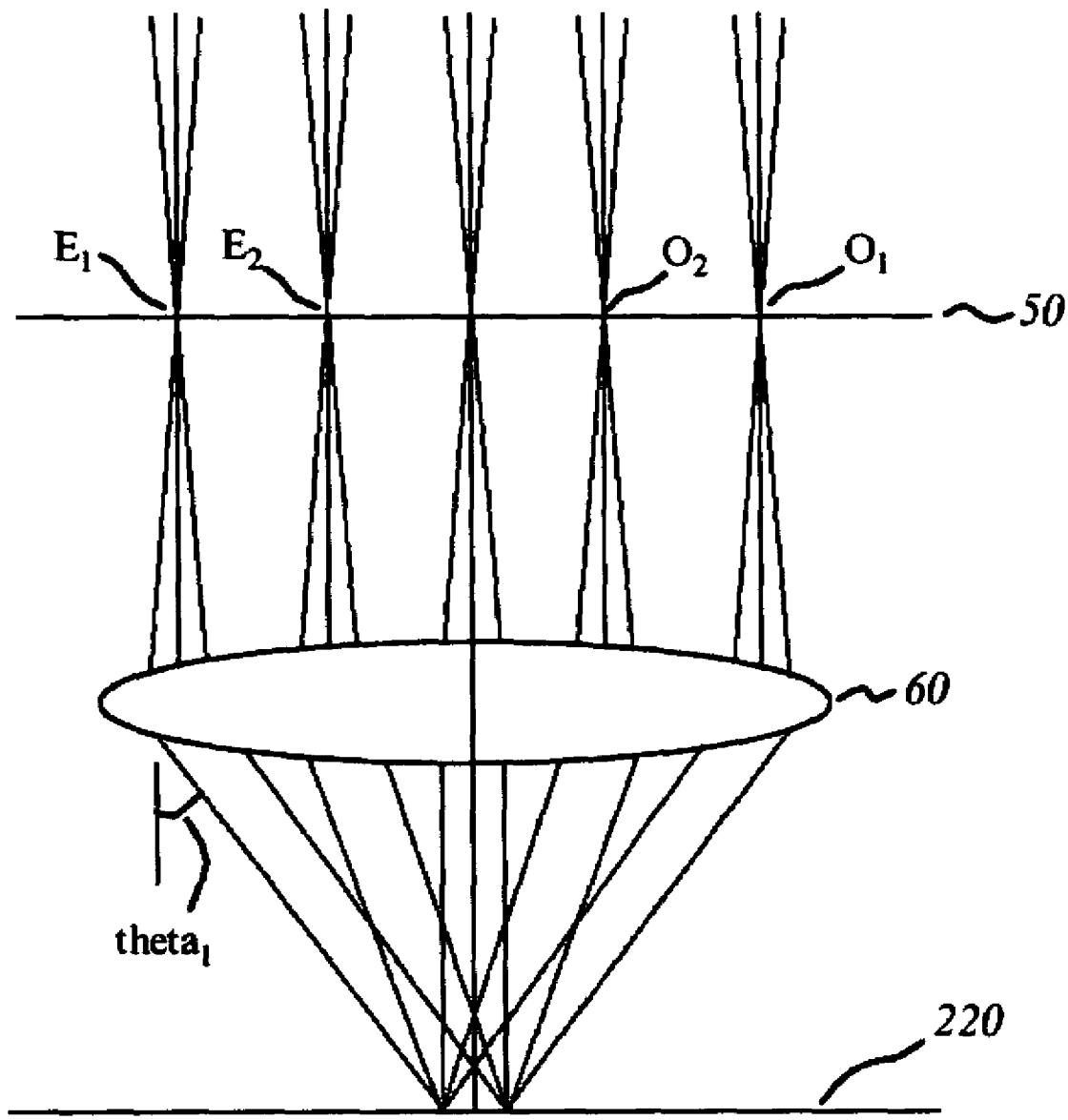
FIG. 3a is a diagram illustrating specular and non-specular reflection in the optical object path of the Mirau interference microscope shown in FIG. 1.
Figure 3B:
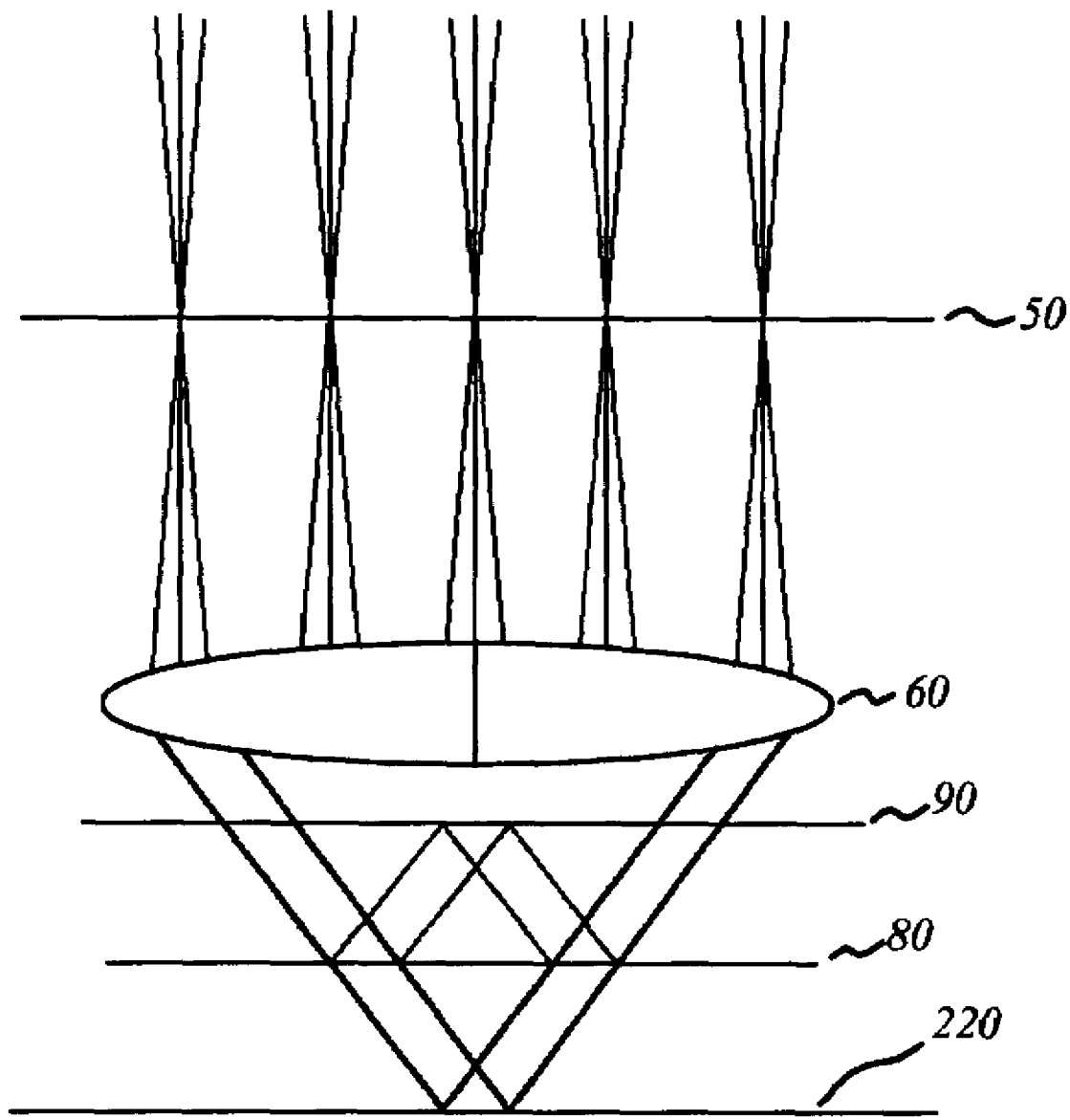
FIG. 3b is a diagram illustrating specular in the optical object path and the optical reference path of the Mirau interference microscope shown in FIG. 1.

The specular and non-specular reflection components can be distinguished at the back focal plane 50. In particular, the mutual coherence function between the object and reference beams at a point on the back focal plane is a function of only the zero-order (specular) reflection term of light scattering off of the object and is not affected by non-specular reflection. This can be appreciated from inspection of FIG. 3a. Referring to FIG. 3a, each point in back focal plane 50 can be considered as a separate source. Consider points $E_1$ and $E_2$ on back focal plane 50. Light from point $E_1$ passes through objective lens 60 and is imaged on object plane 220 at an incident angle ($theta_1$). Specular reflection is reflected from the object at the same angle ($theta_1$), and focused by objective 60 at point $O_1$. Now consider light from point $E_2$. First, no light from $E_2$ that is reflected from the object plane 220 in a specular mode will reach point $O_1$ because it will be reflected from the object plane at a different angle and will be imaged on a different point ($O_2$) on the back focal plane 50. Second, consider light from point $E_2$ that is reflected from the object plane 220 in a non-specular mode. Some of the light from point $E_2$ reflected from the object plane 220 in a non-specular mode may reach point $O_1$. However, this light is incoherent with respect to the light from point $E_1$. Next, consider light from point $E_1$ that is reflected in a non-specular mode from object plane 220. This light will not reach point $O_1$, since by definition, it is reflected at angles other than $theta_1$. Finally, consider light from the reference path that originates at point $E_1$. As illustrated in FIG. 3b, light that follows the reference path is coherent with the light that originates at the same point and passes through the object path. Accordingly, the only light that passes through $O_1$ that is coherent relative to the light reflected from the object in a specular mode is the light from the reference path. This coherency can be distinguished by using interference techniques. Thus, the specularly reflected light can be distinguished from the non-specularly reflected light at the back focal plane by using the fact that it is coherent with the reference beam.

Distinguishing the specularly reflected light at point $O_1$ from the object path that is coherent with respect to the light from point $E_1$ that passes through the reference path is accomplished for each point on the back focal plane by using techniques of interference microscopy.

Consistent with the techniques of interference microscopy, the path-length difference between the reference and object paths is varied. Movement of stage 75 is done is steps short enough to give an accurate representation of the mutual coherence function between the reference channel wave and the object channel wave. This is preferably 1/10 of the shortest wavelength or less.

The image of the back focal plane 50 is captured by video camera 110 as illustrated in FIG. 1. The image of back focal plane 50 of objective lens 60 is imaged onto video camera 110 by post-magnification lens 100. The intensity of the light is sampled for each channel (pixel on video camera image 400) while the path-length difference is varied between the reference and object paths. In the present embodiment, the path length difference is varied by moving the objective lens 60 relative to the object plane. For example, assuming a UV light source of 200 nm, 100 images could be taken at path-length increments of 20 nm.

Figure 4:
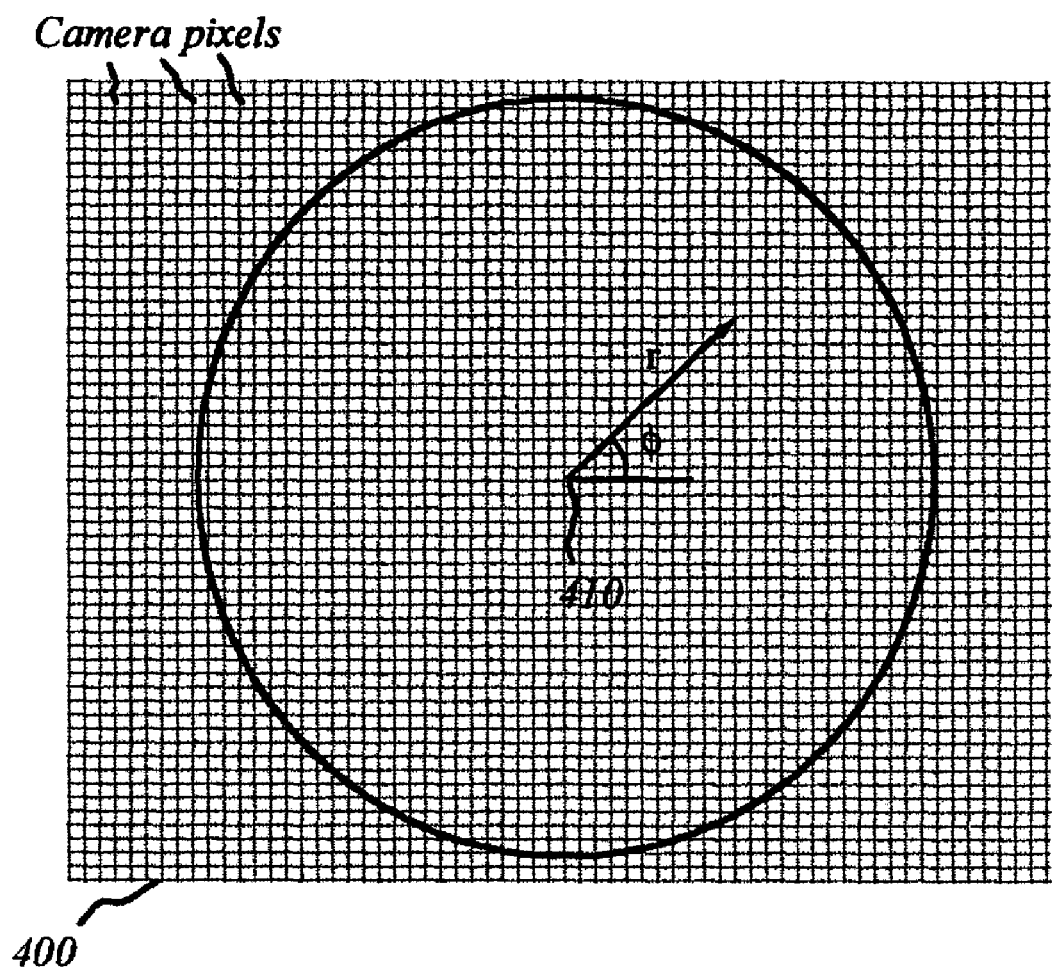
FIG. 4 is an illustration of the image of the back focal plane 50 as captured by video camera 110.
Figure 5:
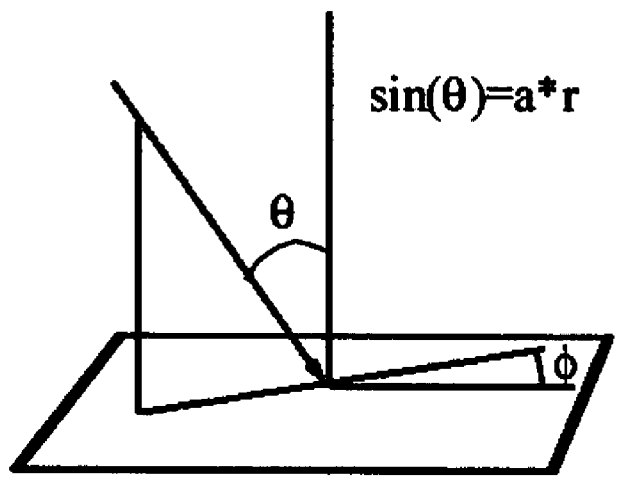
FIG. 5 is an illustration of the scattering angles relative to the object plane 70 showing the relationship to the image on the video camera image 400 illustrated in FIG. 4.

Referring to FIGS. 4 and 5, each pixel detected by video camera 110 is processed as a separate channel and corresponds to a specific angle of incidence of illumination on object plane 70. Specifically, the center point 410 in video camera image 400, illustrated in FIG. 4, corresponds to normal illumination on object plane 70 and points further from center point 410 correspond to increasingly larger scattering angles as illustrated in FIG. 5. To be precise, the radius of a point from the center of the video image is related to the scattering angle of the illumination off of the object by the following mathematical relationship:

Sin (theta)=a*r

Where theta=the scattering angle (relative to normal)

$NA/r_{max}$=a

NA=the numerical aperture of the objective lens

Interference is averaged over a time period that is long (i.e. 1/30 second) relative to the period of the light so that the time average of the light that is not coherent with the reference channel averages to zero. Thus, the captured image of the back focal plane represents only the mutual coherence function between the reference channel wave and the object channel wave.

FIG. 6*a* is an illustration of the intensity data from a typical channel as a function of path-length-difference. Fourier transform spectroscopy techniques are now used to distinguish the specular reflection terms from the non-specular reflection terms. More specifically, the intensity of the light for each channel includes a number of components. However, the non-zero (specular) term can be distinguished from the other terms by taking advantage of the coherency between the reference path and the specular object path for each point on the back focal plane.

The intensity data from each channel is transformed using Fourier transform analysis to obtain as a function of wavelength. FIGS. 6*b* and 6*c* illustrate the real and imaginary parts, respectively, of the Fourier transform of the mutual coherence function of FIG. 6*a*. As is shown mathematically below, the Fourier transform of each channel (intensity as a function of path-length) gives the desired specular reflection information (reflectivity as a function of wavelength). The reflection terms for different scattering angles are obtained from different channels, which provides simultaneous information for different scattering angles. This provides reflectivity data representing the scattering "signature" of the sample.

Other types of interference microscopes can also be adapted in accordance with the present invention. For high numerical aperture applications, the two most suitable interference microscope types are the Linnik microscope and the Mirau microscope. A Mirau interference microscope adapted in accordance with the present invention has been described in detail.

Figure 7:
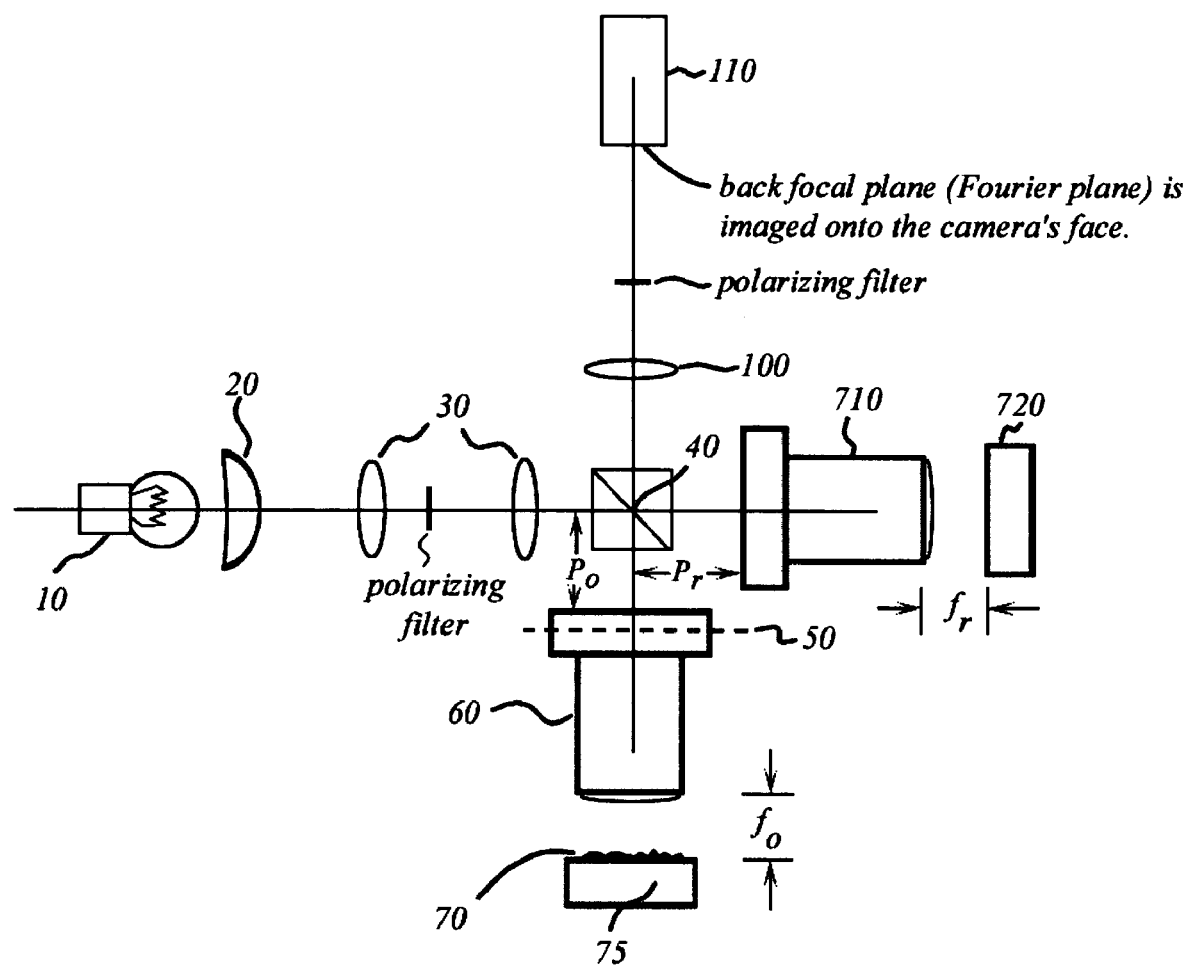
FIG. 7 illustrates a Linnik interference microscope adapted in accordance with the present invention.

A Linnik interference microscope adapted in accordance with the present invention is illustrated in FIG. 7. In this case the reference channel is provided for by having a second reference lens 710, which is as nearly as possible identical to the objective lens 60. The beam splitter 40 splits the illumination into two channels in this case; one directed towards objective lens 60 and the other towards reference lens 710. The light passing through reference lens 710 strikes reference mirror 720 and is specularly reflected back through reference lens 710 to beamsplitter 40 where it recombines with the reflected light from object 70. The superposition of reference channel light and object channel light is detected at by video camera 110. The path length in the Linnik case can be varied by varying any of the dimensions $P_o$, $P_r$, $f_o$, or $f_r$ illustrated in FIG. 7.

Two polarizing filters, one in the illumination channel and one before video camera 110 can be used to collect data, which is polarization sensitive. In the most general configuration the two polarization filters can be rotated about the optical axis.

The interference scatterometry system can efficiently measure the phase and amplitude of the specularly reflected light, as a function of wavelength, angle of incidence, incoming polarization, and detected polarization. This is superior to say an ellipsometer where only the relative phase between two polarizations can be measured, and where only a single angle of incidence can be measured at one time.

Koehler illumination can be achieved with broadband light, but it can also be achieved with narrow band light, so long as the spatial coherence between difference points in the back focal plane of the illumination channel is small when the points are separated by a distance corresponding to a camera pixel or more. Effective Koehler illumination can even by achieved by using a laser illumination system. This can be done by focusing the laser to a small spot on the back focal plane of the illumination system and causing the spot to mechanically scan the back focal plane in a raster mode so as to uniformly fill the back aperture in one camera acquisition frame time. Non-mechanical means of scanning a laser spot are also possible such as electro-optic scanning or acousto-optic scanning.

The Mirau and Linnik interference microscopes have been illustrated with polarizing filters. Polarizing filter 30 is positioned in the illumination path. Polarizing filter 105 is positioned between the back-focal-plane of the objective lens and video camera 110. This allows for measurement of the dependence of reflectivity and complex phase as a function of polarization.

Figure 8:
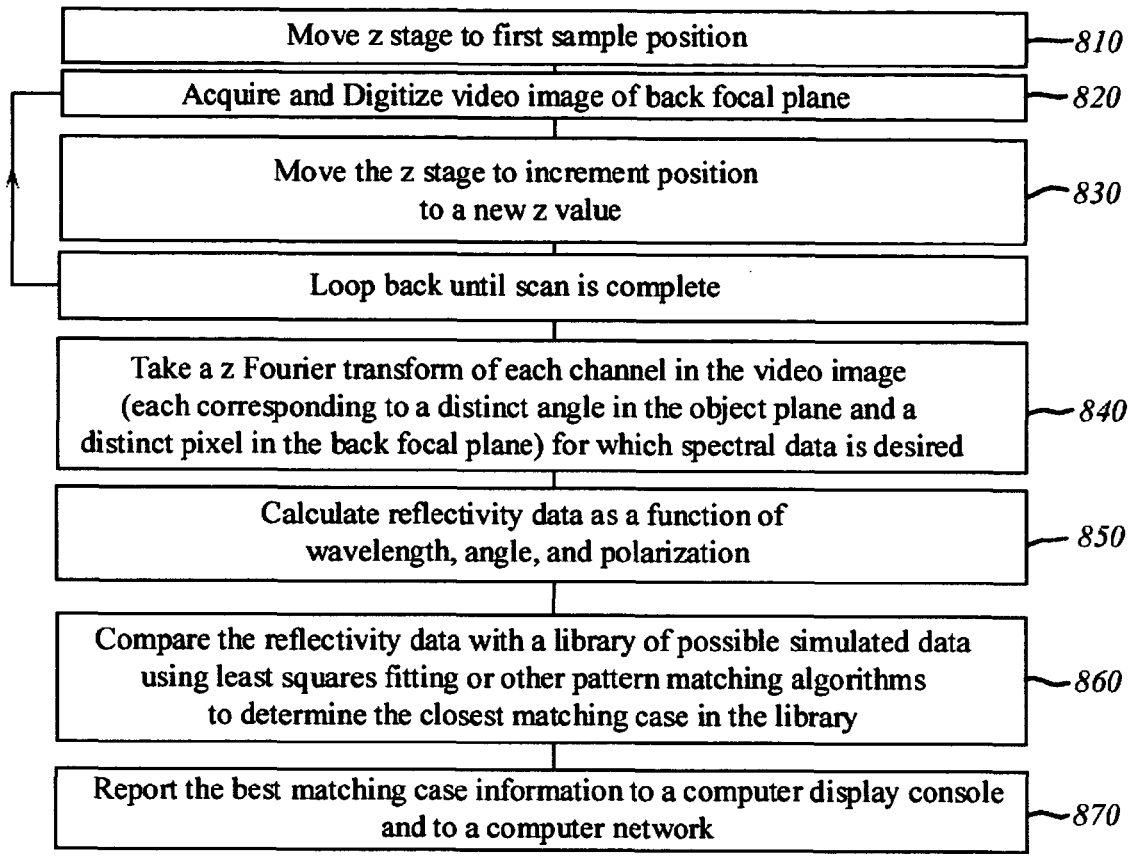
FIG. 8 is an illustration of the sequence of steps used in inverse scattering in accordance with the present invention.

FIG. 8 is an illustration of the sequence of steps used in inverse scattering in accordance with the present invention. In step 810, stage 75 is moved to the first sample position. In step 820, video camera 110 acquires a video image of the back-focal-plane and the image is digitized. In step 830, stage 75 is moved incrementally.

Steps 820 and 830 are then repeated until data is acquired for all stage positions. After data acquisition, step 840 provides a Fourier transform for each channel in the video image. These transforms are used in step 850 to calculate reflectivity data as a function of wavelength, angle and polarization. This reflectivity data is compared to a library of signatures in step 860. The closest fit is reported in step 870 to complete the inverse scattering identification of the physical characteristics of the sample.

MATHEMATICAL ANALYSIS

Given the advanced state of the art of interference microscopy, spectroscopy and Fourier analysis, a mathematical treatment is provided to better explain certain features of the invention to those expert in the art. However, the following explanation is provided only to further the understanding of the invention, and is not intended to be limiting or restrictive in any way.

In the Mirau embodiment (FIG. 1) the image captured by the video camera is that of the back focal plane of the single objective lens. In the Linnik embodiment (FIG. 7) the image captured by the video camera is the common back focal plane images of the two objective lenses. In either a Mirau or Linnik embodiments, the electric field captured by the video camera may be written as a sum or superposition of two electric fields: $E_o$ which comes from light which has traveled through the object channel and $E_r$ which comes from light which has traveled through the reference channel. Both are functions of space and time coordinates:

$$E(x,y,z,t)=E_r(x,y,z,t)+E_o(x,y,z,t) \quad (1)$$

In the case of the Mirau embodiment the object and reference channels both share the same microscope objective lens, whereas in the Linnik design they each have their own distinct microscope objective lens. Other than this physical difference, the two systems are theoretically identical is most respects relevant to the present invention. I use complex notation for the electric fields as is customary in optical literature with the understanding that it is the real part of the field quantities that is the true physical electric field. I shall discuss only the electric fields since the magnetic fields may be derived from the electric fields by using the field equations—Maxwell's equation.

Let the z direction be along the optical axis and perpendicular to the back focal plane's image at the camera face. The coordinates x and y specify the location in the back focal plane. Let the origin in the x-y coordinate system be the optical axis at the camera face. The video camera detects the time-averaged intensity, which we denote by:

$$<E^* \cdot E> = <E_r^* \cdot E_r> + <E_o^* \cdot E_o> + 2Re<E_r^* \cdot E_o> \quad (2)$$

The first two terms on the right hand side of this equation do not depend on the path difference between the object and reference channels. The last term is the interference term and it varies with path-length difference.

The reference mirror in the reference channel is assumed to be an ideal mirror which has only specular reflection and no scattering. The object may of course have scattering in many directions. The typical case in scatterometry is where the object or specimen is repetitive with some spacing parameter like a diffraction grating or a two dimensional field of contact holes.

We now wish to take into account the fact that the specimen needs to be moved along the optical axis, as a sequence of images is captured, and therefore the object field at the camera will depend on the focus coordinate. Let F denote the z coordinate of the highest point in the specimen. Then clearly the object field will depend on this and I can write $$E(x,y,z,t,F)=E_r(x,y,z,t)+E_o(x,y,z,t,F) \quad (3)$$

In a sequence of images I will take measurements at discreet values of F:

$$F=\{F_i\} \quad (4)$$

The simplest choice of sampling in F space is to choose the $F_i$ to be equally spaced, but this is not strictly necessary.

Because the video camera sees an image of the back focal plane, the only term that depends on F to a very good approximation is the mutual coherence cross term $$<E_r^* \cdot E_r> \text{ is independent of F} \quad (5)$$

$$<E_o^* \cdot E_o> \text{ is independent of F} \quad (6)$$

$$<E_r^* \cdot E_o> \text{ is a sensitive function of F} \quad (7)$$

Statement (5) is obviously true, but (6) is not as obvious since $E_o$ depends on F. It nevertheless follows from that fact that since the camera sees the back focal plane, then at any particular pixel in the camera image plane the light arriving at that point from the object channel has scattered off of the specimen into only a single collection angle. It is true that this light can come from several incident illumination directions incident on the specimen, but these must all be added incoherently because of the assumed Koehler illumination condition. As a consequence of this the time average in (6) ends up being independent of the specimen focusing F. If the illumination is only approximately of the Koehler type, which it always is in practice, then the time average in (6) will depend mildly on the focus parameter F. This mild dependence can be either ignored or included as a correction term in a more detailed analysis. So the only term that depends significantly on F is the interference term (7) and we shall discuss this term here.

The complex interference term is a function then of three arguments of the form:

$$<E_r^* \cdot E_o> = C(x,y,F) \quad (8)$$

This is called the mutual coherence function in the back focal plane. We see that it is a function of x, y, and F.

In the reference channel, only specular reflection occurs off of the reference mirror because it is assumed to be an optically flat mirror. Therefore only one angle of incidence for the reference channel illumination contributes to the coherence function C at a given point in the x-y plane. Thus the time-average will integrate to zero all but the scattering from the same illumination ray in the object channel because of the Koehler illumination property that all different angles of illumination of the object are statistically uncorrelated. Thus only the specular reflection of the object ray contributes to the correlation C. As this is an important point, it merits further mathematical elaboration.

Because of Koehler illumination, the phase that each incident plane wave arrives at the specimen is essentially random compared to other rays. We use a discrete Fourier transform representation of the field. So the incident illumination field at the object or specimen has the form:

$$\vec{\mathscr{E}}_{in}(x,y,z,t) = \sum_{k_x}\sum_{k_y}\sum_{k_z} e^{i\phi(k)} e^{i(k \cdot x - \omega(k)t)} V(k) \quad (9)$$

Where the script variable $\xi_{in}$ denotes the field in the neighborhood of the focus plane as opposed to the back focal plane.

$$\omega(k) = c\sqrt{k^2} \tag{10}$$

V(k) is a positive function, and $\Phi(k)$ is the random phase with the following expectations $$\langle e^{i\Phi(k)} \rangle = 0; \langle e^{-i\Phi(k')} e^{i\Phi(k')} \rangle = \delta_{k,k'} \tag{11}$$

$\delta_{k,k'}$ is the Kronecker delta function in the discrete indices of the two wave vectors k and k'.

It is clear that specular reflection is described by the following transformation in k space:

$$k_{out} = (k_x, k_y, -k_z) \tag{12}$$

In other words the z component of the wave vector changes sign. This describes the reference channel. The object channel is more complicated as it involves non-specular scattering in general. Without loss of generality we can write the electric field after scattering off of the object as:

$$\mathscr{E}_o(x,y,z,t) = \sum_{k_{in}} \sum_{k_{out}} \sum_{j,k=1}^{3} e^{i\phi(k_{in})} e^{i(k_{out}\cdot x - \omega(k)t)} \hat{j} S_{j,k}(k_{out}, k_{in}) V_k(k_{in}) \tag{13}$$

Where S is a scattering matrix, and it will depend on the focus position of the object as well as the details of the object's optical properties. Note that all the rays that are scattered from the same incoming plane wave in this expression share the same common random factor.

Several points of clarification are in order regarding equation (13). The first is that evanescent or near field terms have been dropped from this Fourier expansion since these don't radiate and won't be seen by the video camera. The second point is that this expression is an aerial image representation of the scattered light to be understood as the image that would be created of the object in a perfect 1X optical system. This implies that the object has a highest point above which the index of refraction is a constant and typically simply that of a vacuum. The 1X optical system would have the same index of refraction in the object and image planes.

For the reference beam we can write the simpler expression ($S^r$ is the diagonal scattering matrix in this case):

$$\mathscr{E}_r(x,y,z,t) = \sum_{k_{in}} \sum_{j,k=1}^{3} e^{i\phi(k_{in})} e^{i(k_{in}^\% \cdot x - \omega(k)t)} \hat{j} S_{j,k}^r(k_{in}^\%, k_{in}) V_k(k_{in}), \tag{14}$$

$$\text{where } k_{in}^\% = (k_{inx}, k_{iny}, -k_{inz})$$

Let's calculate the mutual coherence between the object and reference waves in the vicinity of the object focus plane. We do this by averaging over the random phases.

$$\langle \mathscr{E}_r^*(x',y',z',t)\mathscr{E}_o(x,y,z,t) \rangle = \tag{15}$$

-continued $$\left\langle \left[ \sum_{k_{in}} \sum_{j,k=1}^{3} e^{i\phi(k_{in})} e^{i(k_{in}^\% \cdot x' - \omega(k)t)} \hat{j} S_{j,k}^r(k_{in}^\%, k_{in}) V_k(k_{in}) \right]^* \times \right.$$
$$\left. \left[ \sum_{k_{in}} \sum_{k_{out}} \sum_{j,k=1}^{3} e^{i\phi(k_{in})} e^{i(k_{out}\cdot x - \omega(k)t)} \hat{j} S_{j,k}(k_{out}, k_{in}) V_k(k_{in}) \right] \right\rangle$$

We now use the results (11). This results in $$\langle \mathscr{E}_r^*(x',y',z',t)\mathscr{E}_o(x,y,z,t) \rangle = \tag{16}$$

$$\sum_{k_{in}} \left\langle \left[ \sum_{j,k=1}^{3} e^{ik_{in}^\% \cdot x'} \hat{j} S_{j,k}^r(k_{in}^\%, k_{in}) V_k(k_{in}) \right]^* \times \right.$$
$$\left. \left[ \sum_{k_{out}} \sum_{j,k=1}^{3} e^{ik_{out}\cdot x} \hat{j} S_{j,k}(k_{out}, k_{in}) V_k(k_{in}) \right] \right\rangle$$

The mutual coherence function is seen to be independent of time, and only values of $k_{out}$ which satisfy $$|k_{out}| = |k_{in}| = |k_{in}^\%| = \frac{2\pi}{\lambda} \tag{14}$$

will contribute.

When this field is imaged in the back focal plane by the object lens optics, all the plane waves that have the same direction for $k_{out}$ will be focused to a single pixel. And moreover, the direction of $k_{out}$ must be the same as $K_{in}^\%$. When this fact is considered along with (14) one sees that the only Fourier term that will contribute at a given pixel in the camera image which is seeing the back focal plane is such that $$k_{out} = K_{in}^\% \tag{15}$$

In other words, only the zero order or specular reflection term contributes to the mutual coherence function in the back focal plane.

Once this simplification is realized, the application of Fourier transform spectroscopy techniques is more or less straightforward. The only point of difference that deserves some consideration is that since the angle of incidence is generally non-normal for most of the rays except the central one, there is a cosine factor that must be included in interpreting the scan data. So that one must factor into Fourier transform the fact that $$k_{outz} = |K_{in}^\%| \cos(\theta) \tag{16}$$

Where $\theta$ is the angle the ray makes with the optical axis. This extra complication is a straightforward matter for those practiced in the state of the art of Fourier transform spectroscopy and won't be considered further her.

Successive video frames are acquired and the focus position is varied as illustrated in FIG. 8. The set of data collected is:

$$C(x_i, y_m, f_n), n=1 \text{ to } N; f_n = f_o + \delta n; \delta \text{ is a scan increment} \tag{17}$$

The scan increment $\delta$ must be small enough to be compatible with the Nyquist sampling criteria to avoid aliasing of the sampled data. The scan range of the focus variable f must be determined by the requirement that the spectral reflectivities which are calculated will be accurately estimated by the techniques of Fourier transform spectroscopy. The standard calculation of reflectivities in this method proceed by taking a discrete Fourier transform of the datasets in the variable f. These Fourier transforms are then related to the spectral reflectivities of the object through standard means.

An alternate embodiment in the Linnik microscope is to move the lens plus reference mirror together along the optical axis holding all the other optical elements fixed. This also achieves a change in path-length, but it makes all the different angles change phase at the same rate, and eliminates the angle dependence in the Fourier transform spectroscopy equations. Theoretically this is an improvement, but in practice it requires more moving parts in the interference microscope, and this can add to cost, complexity, and stability. Still other embodiments for the Linnik system could move any combination of reference mirror, object objective lens, reference objective lens, or beamsplitter to achieve a variation in path difference.

For the Mirau system alternate embodiments include moving any combination of reference mirror, object, and Mirau beamsplitter (the one between the reference mirror and the object) to achieve a path-length difference for use in Fourier transform spectroscopy.

Only exemplary embodiments of the present invention are shown and described in the present disclosure. It is to be understood that the present invention is capable of use in various other combinations and environments and is capable of changes or modifications within the scope of the inventive concept as expressed herein. Further, the description is intended to be descriptive and not limiting. For example, the description of the present invention refers to certain broadband light sources. However, narrow bandwidth sources and "quasi-monochromatic" sources could be used to provide Koehler illumination.

As another example, a laser could be used as the illumination source. This could be a single laser or multiple lasers at different wavelengths. In order to provide the necessary Koehler illumination, the laser (or lasers) are focused to a spot on the back-focal-plane and scanned across the back-focal-plane at a rate of at least once every camera frame. This provides an incoherent source of Koehler illumination.

As a further example, the path-length difference is the preferred embodiment is changed by mechanical means. However, it is possible to vary the path-length difference in other ways without departing from the spirit of the invention. For example, electro-optical devices could be used or the effective path-length could be varied by changing the pressure of the gas along the light paths.

The preferred embodiment of the present invention has been taught in the form of high-NA Linnik and Mirau interference microscopes. However other types of interference microscopes could be adapted in accordance with the teachings herein. Further still, the location of certain optical elements, such as the beamsplitter, could be varied and various adaptations of the interference microscopes could be implemented to vary the path-length differences in alternative ways without departing from the teachings of the invention.

The invention claimed is:

1. An interference scatterometer for providing reflection coefficients as a function of wavelength and angle comprising:

an interference microscope having an object path and a reference path and further including an objective lens with a corresponding back focal plane;

a source for providing Koehler illumination to the back focal plane of the interference microscope objective lens; and a detector positioned to record an optical image of the back focal plane of the objective lens.

2. An interference scatterometer as in claim 1 adapted to illuminate an object at multiple angles.

3. An interference scatterometer as in claim 1 adapted to illuminate an object at multiple angles simultaneously.

4. An interference scatterometer as in claim 1 adapted to illuminate an object at multiple wavelengths.

5. An interference scatterometer as in claim 1 adapted to illuminate an object at multiple wavelengths simultaneously.

6. An interference scatterometer as in claim 1 adapted to illuminate an object at multiple wavelengths and multiple angles.

7. An interference scatterometer as in claim 1 adapted to illuminate an object simultaneously at multiple wavelengths and multiple angles.

8. An interference scatterometer as in claim 1 further comprising apparatus for mechanically varying the path-length difference between the object path and the reference path in the interference microscope.

9. An interference scatterometer as in claim 8 wherein the detector digitizes and records a sequence of optical images of the back focal plane of the objective lens as the path-length difference between the object path and the reference path in the interference microscope is varied.

10. An interference scatterometer as in claim 9 wherein the detector separates the digitized optical images into multiple channels, wherein each channel corresponds to a single location on the back focal plane of the objective lens.

11. An interference scatterometer as in claim 10 further including a processor for performing Fourier transform analysis on multiple channels to determine specular reflection coefficients.

12. An interference scatterometer as in claim 11 wherein the processor performs Fourier transform analysis on multiple channels to determine specular reflection coefficients for multiple angles of illumination.

13. An interference scatterometer as in claim 12 wherein an object is placed at the object plane and the object includes a diffraction grating.

14. An interference scatterometer as in claim 12 further comprising an inverse signature comparator for comparing the specular reflection coefficients to a number of signatures corresponding to known object parameters.

15. An interference scatterometer as in claim 14 wherein the interference microscope is of the Mirau type.

16. An interference scatterometer as in claim 14 wherein the interference microscope is of the Linnik type.

17. An interference scatterometer as in claim 14 wherein a polarizing filter is placed in the illumination channel.

18. An interference scatterometer as in claim 14 wherein a polarizing filter is placed between the back focal plane and the detector.

19. An interference scatterometer as in claim 7 wherein the source is a source of broadband illumination.

20. An interference scatterometer as in claim 7 wherein the source is a source of illumination within a limited bandwidth and the limited bandwidth is less than the bandwidth of the visible spectrum.

21. A method of performing interference scatterometry comprising the steps of:

providing an interference microscope having an object path and a reference path and further having an objective lens with a corresponding back focal plan;

providing Koehler illumination to the back focal plane of the interference microscope objective lens; and detecting an image of the back focal plane of the objective lens.

22. A method as in claim 21 including the further step of mechanically varying the path-length difference between the object path and the reference path in the interference microscope.

23. A method as in claim 21 wherein the step of detecting further includes recording a sequence of optical images of the back focal plane of the objective lens as the path-length difference between the object path and the reference path in the interference microscope is varied.

24. A method as in claim 23 including the further step of separating the sequence of recorded optical images into multiple channels, wherein each channel corresponds to a single location on the back focal plane of the objective lens.

25. A method as in claim 24 including the further step of performing Fourier transform analysis on multiple channels to determine specular reflection coefficients.

26. A method as in claim 25 wherein the step of performing Fourier transform analysis further includes performing Fourier transform analysis on multiple channels to determine specular reflection coefficients for multiple angles of illumination.

27. A method as in claim 26 further including the step of placing an object at the object plane wherein the object includes a diffraction grating.

28. A method as in claim 26 further including the step of performing inverse signature comparison between the specular reflection coefficients and signatures corresponding to known object parameters.

29. A method as in claim 28 wherein the step of providing an interference microscope includes providing an interference microscope of the Mirau type.

30. A method as in claim 28 wherein the step of providing an interference microscope includes providing an interference microscope of the Linnik type.

31. A method as in claim 28 further including the step of providing a polarizing filter in the illumination channel.

32. A method as in claim 28 further including the step of providing a polarizing filter between the back focal plane and the detector.

33. An interference spectrometer as in claim 21 wherein the step of providing Koehler illumination provides broadband illumination.

34. An interference spectrometer as in claim 21 wherein the step of providing Koehler illumination provides illumination provides illumination within a limited bandwidth and the limited bandwidth is less than the bandwidth of the visible spectrum.

* * * * *